United States Patent
Richard et al.

(10) Patent No.: US 7,138,108 B2
(45) Date of Patent: Nov. 21, 2006

(54) PHOTOPROTECTIVE UV-SCREENING COMPOSITIONS COMPRISING (PHENYLSULFONYL) ACRYLONITRILE-SUBSTITUTED SILANES/SILOXANES

(75) Inventors: Hervé Richard, Villepinte (FR); Philippe Breton, Le Chesnay (FR)

(73) Assignee: L'Oreal, Paris (FR)

( * ) Notice: Subject to any disclaimer, the term of this patent is extended or adjusted under 35 U.S.C. 154(b) by 286 days.

(21) Appl. No.: 10/460,195

(22) Filed: Jun. 13, 2003

(65) Prior Publication Data

US 2004/0037791 A1    Feb. 26, 2004

Related U.S. Application Data

(60) Provisional application No. 60/394,659, filed on Jul. 10, 2002.

(30) Foreign Application Priority Data

Jun. 13, 2002  (FR) .................................. 02 07287

(51) Int. Cl.
*A61Q 17/04* (2006.01)
*A61K 8/40* (2006.01)
*A61K 8/46* (2006.01)
*C07F 7/10* (2006.01)

(52) U.S. Cl. ....................... 424/60; 424/59; 424/70.12; 556/415; 558/396

(58) Field of Classification Search ................. 424/59, 424/60, 70.12; 556/415; 558/396
See application file for complete search history.

(56) References Cited

U.S. PATENT DOCUMENTS 5,827,509 A    10/1998    Richard et al.

FOREIGN PATENT DOCUMENTS

EP    0 716 089 A1    6/1996

OTHER PUBLICATIONS

French Search Report issued for FR 02/07287 on Feb. 12, 2003—2 pages.

*Primary Examiner*—Johann Richter
*Assistant Examiner*—Frank Choi
(74) *Attorney, Agent, or Firm*—Buchanan Ingersoll & Rooney, PC

(57) ABSTRACT

Novel (phenylsulfonyl)acrylonitrile siloxanes/silanes, and cosmetic/dermatological sunscreen compositions comprised thereof, are well suited for UV-A photoprotecting the skin and/or the hair against the damaging effects of solar radiation.

23 Claims, No Drawings

PHOTOPROTECTIVE UV-SCREENING COMPOSITIONS COMPRISING (PHENYLSULFONYL) ACRYLONITRILE-SUBSTITUTED SILANES/SILOXANES

CROSS-REFERENCE TO PRIORITY/PROVISIONAL APPLICATIONS

This application claims priority under 35 U.S.C. § 119 of FR-02/07287, filed Jun. 13, 2002, and also claims benefit of provisional application Ser. No. 60/394,659, filed Jul. 10, 2002, both hereby expressly incorporated by reference.

BACKGROUND OF THE INVENTION

1. Technical Field of the Invention

The present invention relates to cosmetic compositions for topical application, in particular intended for photoprotecting the skin and/or the hair, comprising an effective amount of at least one silane or siloxane derivative of (phenylsulfonyl)acrylonitrile, novel silane or siloxane derivatives of (phenylsulfonyl)acrylonitrile, and their uses in cosmetics as UV-A-screening agents.

2. Description of Background/Related/Prior Art

It is known that radiation having wavelengths of between 280 nm and 400 nm allows tanning of the human epidermis, and that radiation having wavelengths of between 280 and 320 nm, known by the name UV-B radiation, causes erythemas and skin burns which can impede the development of natural tanning. For these reasons, and for aesthetic reasons, there is an increasing demand for means for controlling this natural tanning. It is therefore advisable to screen out this UV-B radiation.

It is also known that UV-A rays having wavelengths of between 320 and 400 nm, which cause tanning of the skin, are capable of inducing its impairment, in particular in the case of a sensitive skin or of a skin continually exposed to solar radiation. UV-A rays cause in particular a loss of elasticity of the skin and the appearance of wrinkles which lead to premature skin aging. They promote the onset of the erythematous reaction or amplify this reaction in some subjects and may even be responsible for phototoxic or photoallergic reactions. Thus, for aesthetic and cosmetic reasons such as the preservation of the natural elasticity of the skin, an increasing number of individuals wish to control the effect of UV-A rays on their skin. It is therefore desirable also to screen out UV-A radiation.

Numerous organic compounds intended for protecting the skin from UV-A and/or UV-B radiation have been proposed up until now.

Most of them are aromatic compounds which absorb UV radiation in the region between 280 nm and 315 nm, or in the region between 315 nm and 400 nm and beyond, or in the whole of these regions. They are most often formulated in anti-sun compositions which are provided in the form of oil-in-water or water-in-oil emulsions. Organic screening agents, which are generally lipophilic or hydrophilic, are present in dissolved form, in either of these phases, in appropriate quantities to obtain the desired sun protection factor (SPF).

The expression sun protection factor is understood to mean the ratio of the irradiation time necessary to achieve the erythematogenic threshold in the presence of the screening agent tested to the irradiation time necessary to achieve this same threshold in the absence of screening agent.

In addition to their solar radiation screening power, these photoprotective compounds should also have good cosmetic properties, good solubility in the customary solvents and in particular in fatty substances such as oils and fats, good resistance to water and to perspiration (persistence) and satisfactory photostability.

In this regard, there is known, from the state of the art, in particular from EP-0-716,089 a particularly advantageous family of UV-A-screening agents, consisting of silane or siloxane derivatives of acrylonitrile. These compounds have very good UV-A-screening properties, better solubility in the customary organic solvents and in particular fatty substances such as oils compared with their nonsilicon-containing homologues, and excellent cosmetic properties. However, it has been observed that these UV-A-screening agents had inadequate photostability.

SUMMARY OF THE INVENTION

It has now surprisingly and unexpectedly been determined that a novel family of silane or siloxane derivatives of (phenylsulfonyl)acrylonitrile have screening properties in the UV-A region, solubility in the customary organic solvents and cosmetic properties as efficient as their homologs which are nonphenylsulfonated silicon-containing derivatives of acrylonitrile of the prior art, but which also have, compared with these compounds, a substantially higher photostability.

The present invention thus features silane or siloxane derivatives or mixtures of silane or siloxane derivatives of (phenylsulfonyl)acrylonitrile of formula (1), (2) or (3) which are defined below.

The present invention also features cosmetic compositions for topical application, in particular for photoprotecting the skin and/or the hair, containing, in a cosmetically acceptable carrier, at least one siloxane or silane compound or a mixture of siloxane or silane compounds derived from (phenylsulfonyl)acrylonitrile of formula (1), (2) or (3) which are defined below.

This invention also features a regime or regimen comprising administering the compounds of formula (1), (2) or (3) in a cosmetic composition for protecting the skin and/or the hair against solar radiation as UV-A-screening agent.

The siloxane or silane derivatives of (phenylsulfonyl) acrylonitrile, in isolated form or in the form of a mixture, correspond to one of the following general formulae (1), (2) or (3):

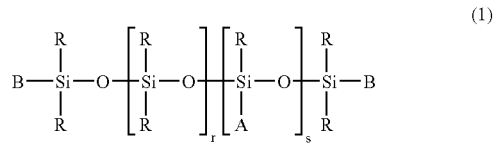

(1)

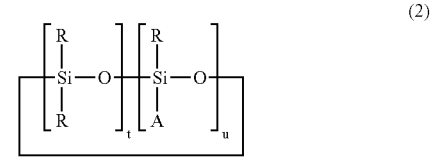

(2)

(3)

in which:

A is a radical of the following formula (I):

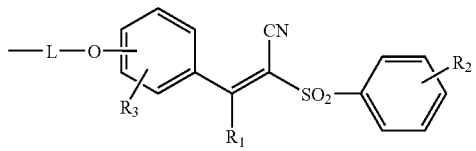

(I)

$R_1$ is a hydrogen atom; a saturated or unsaturated, linear or branched $C_1$–$C_8$ alkyl radical; a phenyl radical which is optionally substituted with one or more saturated or unsaturated, linear or branched $C_1$–$C_8$ alkyl or alkoxy radicals, $R_2$ is a hydrogen atom; a saturated or unsaturated, linear or branched $C_1$–$C_8$ alkyl radical; a saturated or unsaturated, linear or branched $C_1$–$C_8$ alkoxy radical, $R_3$ is a saturated or unsaturated, linear or branched $C_1$–$C_8$ alkyl radical; a saturated or unsaturated, linear or branched $C_1$–$C_8$ alkoxy radical;

L is a divalent radical allowing the attachment of the radical A onto the silicone chain chosen from methylene, ethylene or a group corresponding to one of the following formulae (a), (a') or (a"):

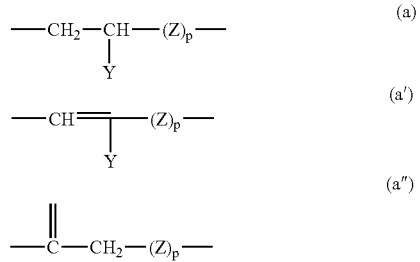

in which:

Z is a saturated or unsaturated, linear or branched $C_1$–$C_6$ alkylene radical optionally substituted with a hydroxyl radical or a saturated or unsaturated, linear or branched $C_1$–$C_8$ alkyl radical, Y represents a hydrogen atom; a hydroxyl radical or a saturated or unsaturated, linear or branched $C_1$–$C_8$ alkyl radical, p is 0 or 1, the radicals R, which are identical or different, denote a saturated or unsaturated, linear or branched $C_1$–$C_{20}$ alkyl group, a phenyl group, a 3,3,3-trifluoropropyl group or a trimethylsilyloxy group; at least 80% in numerical terms of the radicals R being methyl, the radicals B, which are identical or different, are chosen from the radicals R and the radical A, r is a number varying from 0 to 50, s is a number varying from 0 to 20 and if s is 0, at least one of the two symbols B is A, u is a number varying from 1 to 6 inclusive, t is a number varying from 0 to 10;

t+u is greater than or equal to 3;

$R'_1$, $R'_2$, $R'_3$, which are identical or different, are chosen from saturated or unsaturated, linear or branched $C_1$–$C_8$ alkyl radicals; the phenyl radical or the benzyl radical.

DETAILED DESCRIPTION OF BEST MODE AND SPECIFIC/PREFERRED EMBODIMENTS OF THE INVENTION

Although in formula (I) above, only the isomers in which the cyano substituent is in the cis position with respect to the alkoxyphenyl substituent are represented, this formula should be understood also to encompass the corresponding trans isomer.

In the above formulae (1) to (3), the alkyl radical may be linear or branched, saturated or unsaturated and may be chosen in particular from the methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical which is particularly preferred is the methyl radical.

In the above formulae (1) to (3), the alkoxy radicals may be linear or branched and may be chosen in particular from the methoxy, ethoxy, n-propoxy, isopropoxy, n-butoxy and isobutoxy radicals. The alkoxy radical which is particularly preferred is the methoxy radical.

The linear or cyclic diorganosiloxanes of formula (1) or (2) falling within the scope of the present invention are oligomers or random polymers preferably having at least one, and still more preferably all, of the following characteristics:

R is alkyl and still more preferably methyl,

B is alkyl and still more preferably methyl (case of the linear compounds of formula (1)), r varies from 0 to 10 inclusive; s varies from 0 to 6 inclusive (case of the linear compounds of formula (1)), t+u is from 3 to 5 (case of the cyclic compounds of formula (2)), $R_1$ is H, $R_2$ is H, $R_3$ is H, p equals 1, Z is $CH_2$, Y is H or $CH_3$.

Among the diorganosiloxanes of formula (1) which are more particularly preferred, there may be mentioned:

[4-[2-methyl-3-[1,3,3,3-tetramethyl-1-[(trimethylsilyl)oxy] disiloxanyl]propyloxy]phenyl]-2-(benzenesulfonyl)acrylonitrile (compound A) having the structure:

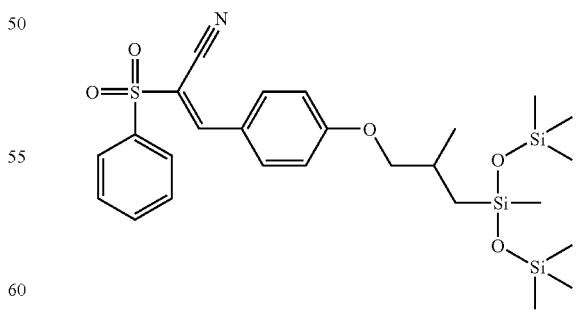

(compound A)

a mixture of [4-[3-[1,3,3,3-tetramethyl-1-[(trimethylsilyl) oxy]disiloxanyl]-2-propenoxy]phenyl]-2-(benzenesulfonyl)acrylonitrile (compound B) and [4-[2-[1,3,3,3-tetramethyl-1-[(trimethylsilyl)oxy]-disiloxanyl]-2-propenoxy] phenyl]-2-(benzenesulfonyl)-acrylonitril e (compound C)

having the following structures (and more particularly whose compound B/compound C molar ratio is 33/67):

(compound B)

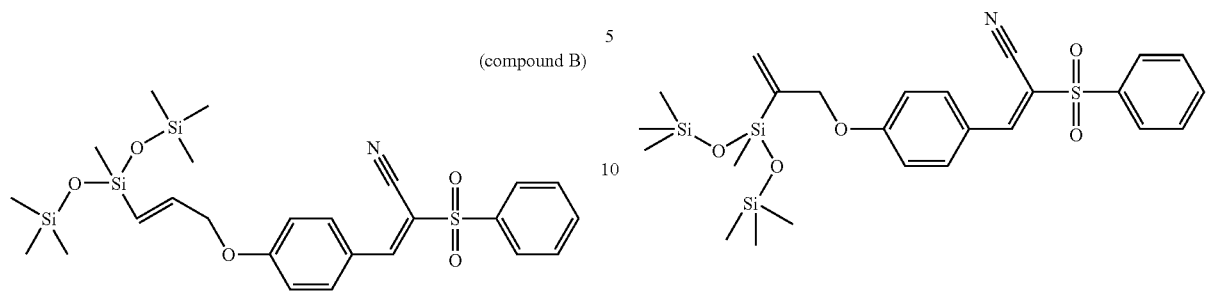

(compound C)

a mixture of 3α,ω-polydimethylsiloxanes (compounds D, E, F) carrying 2 groups 4-(2-propenoxyphenyl)-2-(benzenesulfonyl)acrylonitrile and/or 4-(3-propenoxyphenyl)-2-(benzenesulfonyl)acrylonitrile having the following structures:

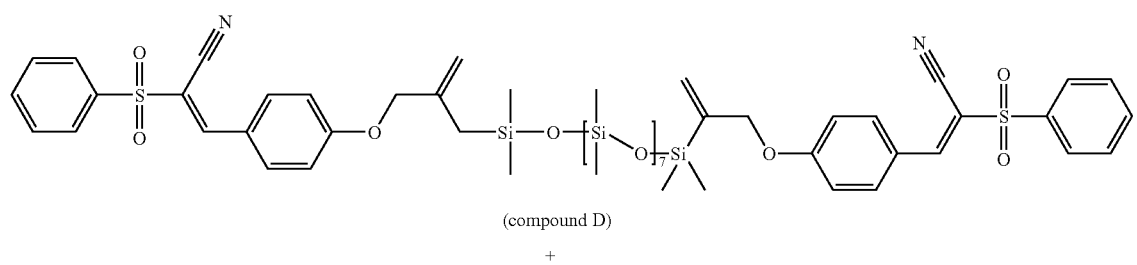

(compound D)

+

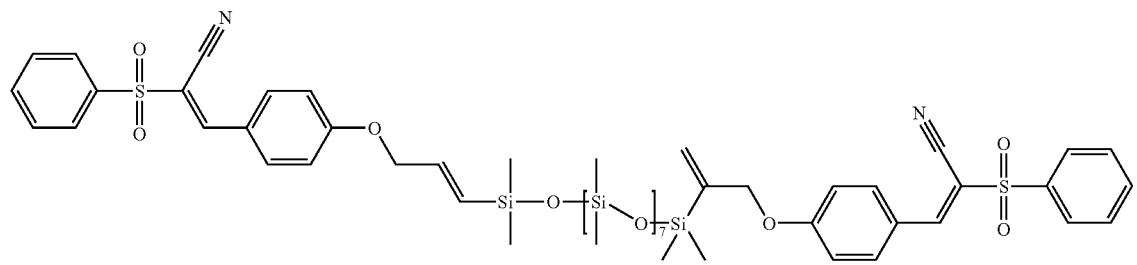

(compound E)

+

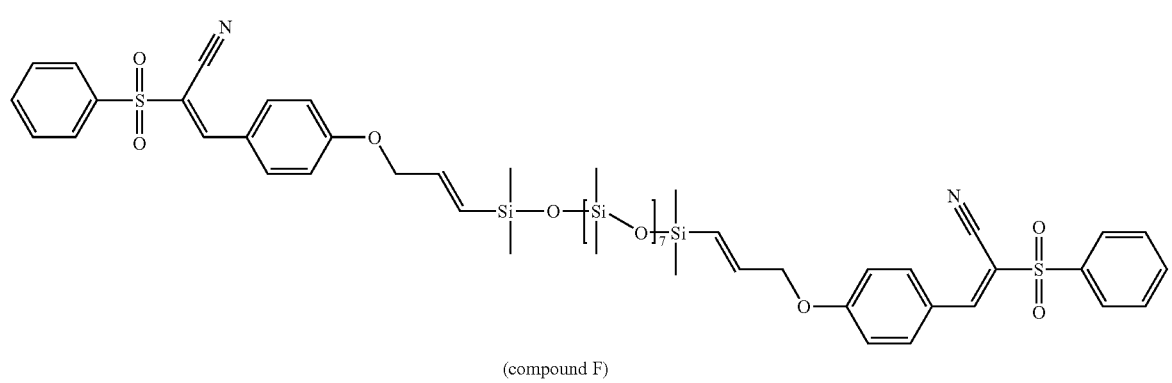

(compound F)

The silane compounds of formula (3) falling within the scope of the present invention preferably have at least one, and still more preferably all, of the following characteristics:

$R'_1$ is methyl,
$R'_2$ is methyl,
$R'_3$ is methyl,
$R_1$ is H,
$R_2$ is H,
$R_3$ is H,
p equals 1,
Z is $CH_2$,
Y is H or $CH_3$.

Among the silane compounds of formula (3) which are more particularly preferred, there may be mentioned 2-benzenesulfonyl-3-[4-(3-trimethylsilanylpropoxy)phenyl]acrylonitrile having the following structure:

(compound G)

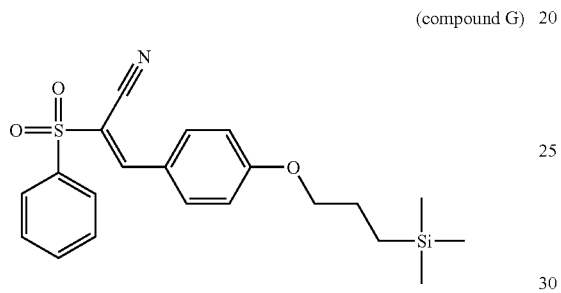

To prepare the derivatives of formula (1) or (2), the procedure may be carried out conventionally using a hydrosilylation reaction starting with the corresponding siloxane derivative in which, for example, all the radicals A are hydrogen atoms. This derivative is called in the text that follows SiH-containing derivative.

The SiH groups may be present in the chain and/or at the chain ends. These SiH-containing derivatives are products which are well known in the silicone industry and are generally commercially available. They are, for example, described in U.S. Pat. Nos. 3,220,972, 3,697,473 and 4,340,709.

The SiH-containing derivatives corresponding respectively to the compounds of formulae (1) and (2) may therefore be represented by the following formulae (4) and (5).

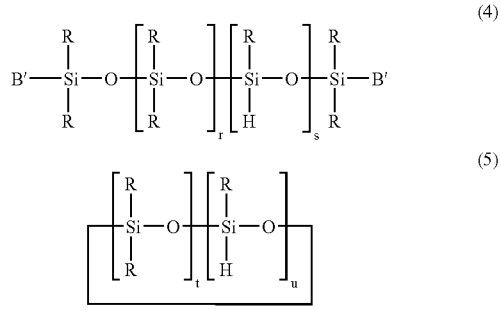

in which:
R, r, s, t and u have the meaning given above for the formulae (1) and (2), B', which are identical or different, are chosen from the radicals R and a hydrogen atom.

In order to prepare the siloxane compounds of the invention of formulae (1) or (2) above, the procedure is carried out in the following manner: (scheme 1): on the corresponding SiH-containing derivative of formula (4) or (5), there is performed a hydrosilylation reaction in the presence of a catalytically effective quantity of a platinum catalyst on an organic derivative of (phenylsulfonyl)-acrylonitrile of the following formula (I'):

Scheme 1

(4) or (5)  +

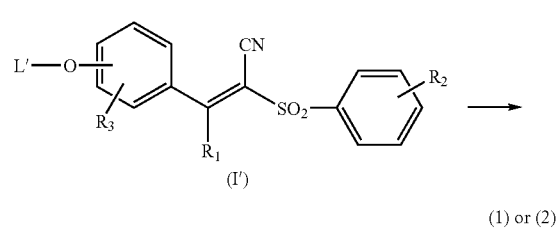

(1) or (2)

in which $R_1$, $R_2$ and $R_3$ have the same meaning as in formula (I) above and L' corresponds to one of the following two formulae (b) and (b'):

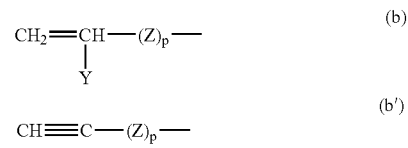

in which Y, Z, p and q have the same meanings as in the formulae (a) and (a') above.

The hydrosilylation reaction is therefore carried out according to one of the following two reactions:

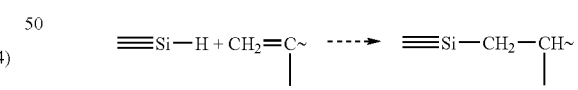

(grafting onto the formula (b)) or

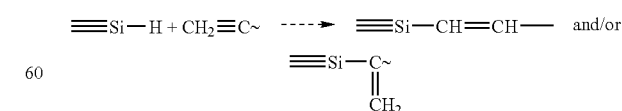

(grafting onto the formula (b'))

The derivatives of formula (I') are obtained by condensing an alkene or alkenyl halide with a derivative of formula (I"):

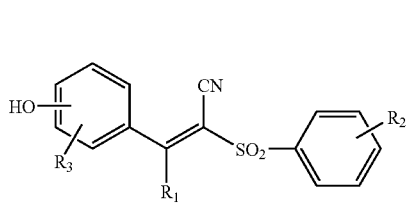

in which the radicals $R_1$, $R_2$ and $R_3$ have the same meaning as in the preceding formulae (I) and (I').

The derivatives of formula (I") are obtained by condensing an aromatic hydroxybenzaldehyde or a hydroxyphenone with a (phenylsulfonyl)acetonitrile in toluene in the presence of piperidinium acetate as catalyst (Knoevenagel condensation) according to the following scheme:

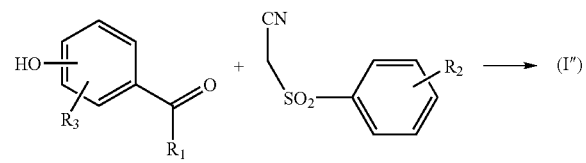

in which the radicals $R_1$, $R_2$ and $R_3$ have the same meaning as in the formulae (I) and (I').

As aromatic benzaldehyde derivatives, there may be mentioned 4-hydroxybenzaldehyde or vanillin which are commercial products. As phenone derivative, there may be mentioned 4-hydroxyacetophenone.

As (phenylsulfonyl)acetonitrile derivative, there may be mentioned (benzenesulfonyl)acetonitrile which is a commercial product.

To prepare the silane derivatives of formula (3), one of the following two schemes may be used:

(A) Route where a halogenated silane derivative is reacted with an aromatic hydroxybenzaldehyde or a hydroxyphenone in the presence of a base (conventional alkylation reaction), the benzaldehyde or phenone obtained being condensed with a (phenylsulfonyl)acetonitrile in toluene in the presence of piperidinium acetate as catalyst (Knoevenagel condensation) according to the following scheme 2:

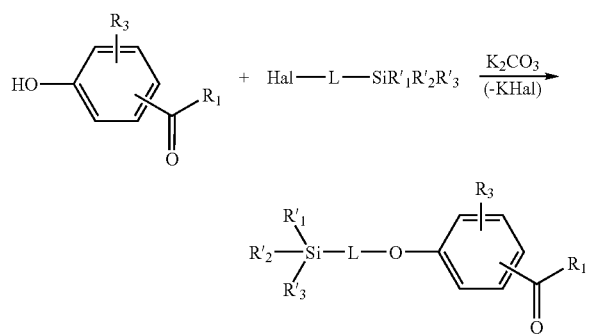

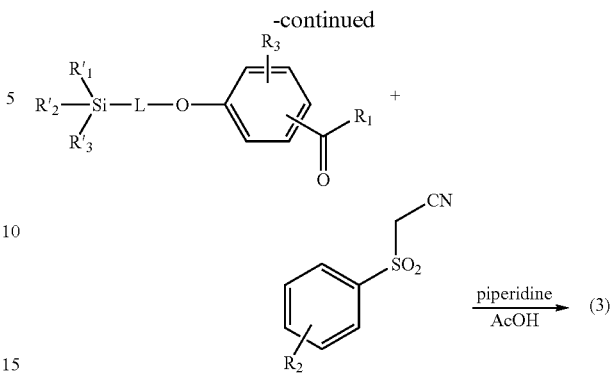

in which L, $R'_1$ to $R'_3$ and $R_1$ to $R_3$ have the meanings indicated above for the formulae (3) and (I) defined above and Hal represents a halogen and more particularly chlorine.

(B) Route which consists in starting with the derivative of the following formula (6) in which $R_1$ to $R_3$ have the same meanings as in formula (I) above and reacting with it, in the presence of a base (conventional alkylation reaction), the derivative of formula (7) in which L, $R'_1$ to $R'_3$ have the same definition as in formula (3) above and Hal represents a halogen and more particularly chlorine according to the following scheme:

Scheme 3

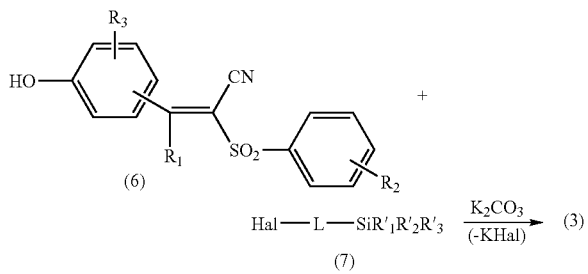

As silane halide derivatives, there may be mentioned chloropropyltrimethylsilane or chloromethyltrimethylsilane sold by WACKER. The compounds used in the compositions according to the invention have good fat-solubility and may thus be used at high concentrations in the cosmetic compositions, which can confer a very high protection value on the compositions containing them. Moreover, this good solubility causes them to become uniformly distributed in conventional cosmetic carriers containing at least one fatty phase or one cosmetically acceptable organic solvent and may thus be applied to the skin or the hair to form an effective protective film.

As indicated above, the compounds of formulae (1), (2) or (3) have an excellent screening power in the UV-A range, that is to say in the domain having wavelengths ranging from 320 nm to 400 nm, and have a satisfactory photostability.

The compound(s) of formula (1), (2) or (3) are preferably present in the cosmetic compositions for topical use of the present invention in an amount of 0.1% to 20% by weight, and in particular in an amount of 0.5 to 10% by weight, relative to the total weight of the cosmetic composition.

The cosmetic, in particular anti-sun, compositions of the present invention may contain, in addition, one or more additional organic sunscreens which are active in the UV-A and/or UV-B domain.

The additional organic UV-screening agents in accordance with the invention may be water-soluble, fat-soluble or insoluble in the customary cosmetic solvents. They are chosen in particular from anthranilates; cinnamic derivatives; dibenzoylmethane derivatives; salicylic derivatives, camphor derivatives; triazine derivatives such as those disclosed in U.S. Pat. No. 4,367,390, EP-863,145, EP-517,104, EP-570,838, EP-796,851, EP-775,698, EP-878,469 and EP-933,376; benzophenone derivatives, in particular those disclosed in EP-A-1-046,391 and DE-1-0012408; β,β'-diphenyl acrylate derivatives, benzotriazole derivatives, benzimidazole derivatives; imidazolines; bis-benzoazolyl derivatives as disclosed in EP-669,323 and U.S. Pat. No. 2,463,264; p-aminobenzoic acid (PABA) derivatives; methylenebis(hydroxyphenyl-benzotriazole) derivatives as disclosed in U.S. Pat. Nos. 5,237,071, 5,166,355, GB-2-303, 549, DE-1-9726184 and EP-893,119; screening polymers and screening silicones such as those disclosed in WO 93/04665; dimers derived from α-alkylstyrene such as those disclosed in DE-1-9855649; 4,4-diarylbutadiene derivatives such as those disclosed in EP-0-967,200, DE-1-9746654, DE-1-9755649, EP-A-1008586, EP-1-133 and EP-1-133, 981 and their mixtures.

As examples of additional organic screening agents, there may be mentioned those designated below under their INCI name:

para-Aminobenzoic Acid Derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF,
Salicylic Derivatives:
Homosalate sold under the name "Eusolex HMS" by Rona/EM Industries,
Ethylhexyl Salicylate sold under the name "NEO HELIOPAN OS" by Haarmann and REIMER,
Dipropyleneglycol Salicylate sold under the name "DIPSAL" by SCHER,
TEA Salicylate, sold under the name "NEO HELIOPAN TS" by Haarmann and REIMER,
Dibenzoylmethane Derivatives:
Butyl Methoxydibenzoylmethane sold in particular under the trademark "PARSOL 1789" by HOFFMANN LA ROCHE, Isopropyl Dibenzoylmethane,
Cinnamic Derivatives:
Ethylhexyl Methoxycinnamate sold in particular under the trademark "PARSOL MCX" by HOFFMANN LA ROCHE,
Isopropyl Methoxy cinnamate,
Isoamyl Methoxy cinnamate sold under the trademark "NEO HELIOPAN E 1000" by HAARMANN and REIMER,
Cinoxate,
DEA Methoxycinnamate,
Diisopropyl Methylcinnamate,
Glyceryl Ethylhexanoate Dimethoxycinnamate,
) β,β'-Diphenyl Acrylate Derivatives:
Octocrylene sold in particular under the trademark "UVINUL N539" by BASF, Etocrylene, sold in particular under the trademark "UVINUL N35" by BASF,
Benzophenone Derivatives:
Benzophenone-1 sold under the trademark "UVINUL 400" by BASF,
Benzophenone-2 sold under the trademark "UVINUL D50" by BASF,
Benzophenone-3 or Oxybenzone, sold under the trademark "UVINUL M40" by BASF,
Benzophenone-4 sold under the trademark "UVINUL MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "UVINUL DS-49" by BASF,
Benzophenone-12, n-Hexyl 2-(4-diethylamino-2-hydroxybenzoyl)benzoate,
Benzylidenecamphor Derivatives:
3-Benzylidene camphor manufactured under the name "MEXORYL SD" by CHIMEX,
4-Methylbenzylidene camphor sold under the name "EUSOLEX 6300" by MERCK,
Benzylidene Camphor Sulfonic Acid manufactured under the name "MEXORYL SL" by CHIMEX,
Camphor Benzalkonium Methosulfate manufactured under the name "MEXORYL SO" by CHIMEX,
Terephthalylidene Dicamphor Sulfonic Acid manufactured under the name "MEXORYL SX" by CHIMEX,
Polyacrylamidomethyl Benzylidene Camphor manufactured under the name "MEXORYL SW" by CHIMEX,
Phenylbenzimidazole Derivatives:
Phenylbenzimidazole Sulfonic Acid sold in particular under the trademark "EUSOLEX 232" by MERCK,
Disodium Phenyl Dibenzimidazole Tetra-sulfonate sold under the trademark "NEO HELIOPAN AP" by Haarmann and REIMER,
Triazine Derivatives:
Anisotriazine sold under the trademark "TINOSORB S" by CIBA GEIGY,
Ethylhexyl triazone sold in particular under the trademark "UVINUL T150" by BASF,
2,4,6-Tris(diisobutyl 4'-aminobenzalmalonate)-s-triazine,
Diethylhexyl Butamido Triazone sold under the trademark "UVASORB HEB" by SIGMA 3V,
Phenylbenzotriazole Derivatives:
Drometrizole Trisiloxane sold under the name "Silatrizole" by RHODIA CHIMIE,
Methylene bis-Benzotriazolyl Tetramethylbutylphenol, sold in solid form under the trademark "MIXXIM BB/100" by FAIRMOUNT CHEMICAL or in micronized form in aqueous dispersion under the trademark "TINOSORB M" by CIBA SPECIALTY CHEMICALS,
Anthranilic Derivatives:
Menthyl anthranilate sold under the trademark "NEO HELIOPAN MA" by Haarmann and REIMER,
Imidazoline Derivatives:
Ethylhexyl Dimethoxybenzylidene Dioxoimidazoline Propionate,
Benzalmalonate Derivatives:
Polyorganosiloxane with benzmalonate functional groups as the Polysilicone-15 sold under the trademark "PARSOL SLX" by HOFFMANN LA ROCHE 4,4-diarylbutadiene Derivatives:
1,1-dicarboxy (2,2'-dimethyl-propyl)-4,4-diphenylbutadiene and mixtures thereof.

The additional organic UV-screening agents which are more particularly preferred are chosen from the following compounds:
Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Disodium Phenyl Dibenzimidazole Tetra-sulfonate,
Anisotriazine,
Ethylhexyl triazone,
Diethylhexyl Butamido Triazone,
2,4,6-Tris(diisobutyl 4'-aminobenzalmalonate)-s-triazine,
Methylene bis-Benzotriazolyl Tetramethylbutylphenol,
Drometrizole Trisiloxane,
Polysilicone-15
1,1-dicarboxy (2,2'-dimethyl-propyl)-4,4-diphenylbutadiene and mixtures thereof.

The additional UV-screening agents in accordance with the invention are generally present in the compositions according to the invention in proportions ranging from 0.1% to 20% by weight relative to the total weight of the composition, and preferably ranging from 0.2% to 15% by weight relative to the total weight of the composition.

The cosmetic compositions according to the invention may contain, in addition, one or more inorganic pigments and in particular nanopigments of metal oxides, coated or otherwise, such as for example nanopigments of titanium oxide in amorphous or crystallized form (rutile and/or anatase), of iron oxide, of zinc oxide, of zirconium oxide or of cerium oxide. These nanopigments have a mean particle size of between 5 nm and 100 nm, preferably between 10 nm and 50 nm and are all known UV photoprotective agents.

These nanopigments may be coated with known coating agents such as for example alumina and/or aluminum stearate. Such coated or uncoated nanopigments are disclosed, for example, in EP-A-0-518,772 and EP-A-0-518,773.

The cosmetic compositions according to the invention may contain, in addition, agents for artificially bronzing and/or tanning the skin (self-tanning agents) such as dihydroxyacetone (DHA).

The compositions in accordance with the present invention may comprise, in addition, conventional cosmetic adjuvants chosen in particular from fatty substances, organic solvents, ionic or nonionic thickeners, demulcents, humectants, antioxidants, moisturizers, desquamating agents, anti-free-radical agents, antipollution agents, antibacterials, anti-inflammatory agents, depigmenting agents, propigmenting agents, opacifiers, stabilizers, emollients, silicones, antifoaming agents, insect repellents, perfumes, preservatives, anionic, cationic, nonionic, zwitterionic or amphoteric surfactants, substance P antagonists, substance CGRP antagonists, fillers, pigments, polymers, propellants, alkalinizing or acidifying agents or any other ingredient normally used in the cosmetic and/or dermatological field.

The fatty substances may consist of an oil or a wax or mixtures thereof. The expression oil is understood to mean a compound which is liquid at room temperature. The expression wax is understood to mean a compound which is solid or substantially solid at room temperature, and whose melting point is generally greater than 35° C.

As oils, there may be mentioned mineral oils (paraffin); vegetable oils (sweet almond, macadamia, blackcurrant seed or jojoba oil); synthetic oils such as perhydrosqualene, fatty alcohols, acids or esters (such as $C_{12}$–$C_{15}$ alcohol benzoate sold under the trademark "Finsolv TN" by the company WITCO, octyl palmitate, isopropyl lanolate, triglycerides including those of capric/caprylic acids), oxyethylenated or oxypropylenated fatty esters and ethers; silicone oils (cyclomethicone, polydimethylsiloxanes or PDMS) or fluorinated oils, polyalkylenes.

As waxy compounds, there may be mentioned paraffin, carnauba wax, beeswax, hydrogenated castor oil.

Among the organic solvents, there may be mentioned lower alcohols and polyols. The latter may be chosen from glycols and glycol ethers such as ethylene glycol, propylene glycol, butylene glycol, dipropylene glycol or diethylene glycol.

The thickeners may be chosen in particular from crosslinked polyacrylic acids, acrylamidomethylpropanesulfonic acid (AMPS) polymers such as polyacrylamide/isoparaffin/laureth-7 (Sepigel 305), stearic acid, fatty alcohols, xanthan gums, guar gums and modified or unmodified celluloses such as hydroxypropylated guar gum, methylhydroxyethylcellulose and hydroxypropylmethylcellulose.

Of course, persons skilled in the art will be careful to choose the possible additional compound or compounds cited above and/or their quantities such that the advantageous properties intrinsically attached to the compounds in accordance with the invention are not, or not substantially, impaired by the addition(s) envisaged.

The compositions according to the invention may be prepared according to techniques well known to persons skilled in the art, in particular those intended for the preparation of oil-in-water or water-in-oil type emulsions.

This composition may be provided in particular in the form of a simple or complex emulsion (O/W, W/O, O/W/O or W/O/W) such as a cream or a milk, in the form of a gel or a gel cream, or in the form of a lotion, a powder or a solid stick, and may be optionally packaged as an aerosol and may be provided in the form of a mousse or a spray.

Preferably, the compositions according to the invention are provided in the form of an oil-in-water or water-in-oil emulsion.

When it is an emulsion, the aqueous phase thereof may comprise a nonionic vesicular dispersion prepared according to known methods (Bangham, Standish and Watkins. J. Mol. Biol. 13, 238 (1965), FR-2-315,991 and FR-2-416,008).

When the cosmetic composition according to the invention is used for the care of the human epidermis, it may be provided in the form of a suspension or a dispersion in solvents or fatty substances, in the form of a nonionic vesicular dispersion or in the form of an emulsion, preferably of the oil-in-water type, such as a cream or a milk, in the form of an ointment, a gel, a gel cream, a solid stick, a powder, an aerosol mousse or a spray.

When the cosmetic composition according to the invention is used for hair care, it may be provided in the form of a shampoo, a lotion, a gel, an emulsion, a nonionic vesicular dispersion and may constitute, for example, a rinse-out composition to be applied before or after shampooing, before or after dyeing or bleaching, or before, during or after permanent waving or hair straightening, a hair styling or treatment lotion or gel, a blow drying or hair setting lotion or gel, a composition for permanent waving or straightening, dyeing or bleaching the hair.

When the composition is used as a makeup product for the nails, the lips, the eyelashes, the eyebrows or the skin, such as a treatment cream for the epidermis, a foundation, a lipstick, an eyeshadow, a blusher, a mascara or an eyeliner, it may be provided in an anhydrous or aqueous, solid or pasty form, such as oil-in-water or water-in-oil emulsions, nonionic vesicular dispersions or suspensions.

As a guide, for the anti-sun formulations in accordance with the invention which have a carrier of the oil-in-water emulsion type, the aqueous phase (comprising in particular the hydrophilic screening agents) generally represents from 50% to 95% by weight, preferably from 70% to 90% by weight, relative to the whole formulation, the oily phase (comprising in particular the lipophilic screening agents) from 5% to 50% by weight, preferably from 10% to 30% by weight, relative to the whole formulation, and the (co) emulsifier(s) from 0.5% to 20% by weight, preferably from 2% to 10% by weight, relative to the whole formulation.

In order to further illustrate the present invention and the advantages thereof, the following specific examples are given, it being understood that same are intended only as illustrative and in nowise limitative.

EXAMPLES OF PREPARATION

Example 1

Synthesis of 2-benzenesulfonyl-3-[4-(3-trimethylsilanylpropoxy)phenyl]acrylonitrile (Compound G) of Formula (3) (with $R'_1$ to $R'_3$=$CH_3$, $R_1$ to $R_3$=H, L is of Formula (a) with Y=H, Z=$CH_2$ and p=1):

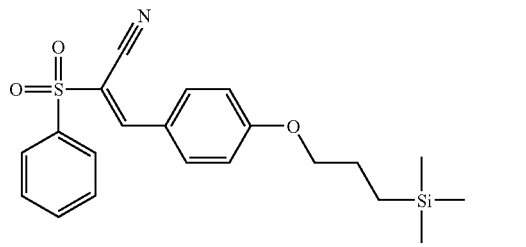
(compound G)

a) First Step: Preparation of 4-(3-trimethylsilanylpropyloxy) benzaldehyde:

3-Chloropropyltrimethylsilane (33.14 g, 0.22 mol) is added dropwise, over 10 minutes, to a mixture of 4-hydroxybenzaldehyde (24.4 g, 0.2 mol) and of potassium carbonate (30.4 g, 0.22 mol) in 150 ml of dry DMF heated to 120° C. under nitrogen. The reaction mixture is left for 2 hours 30 minutes at 120–130° C. It is cooled and poured into ice-cold water. The aqueous phase is extracted 3 times with dichloromethane. The organic phases are dried over sodium sulfate and concentrated under vacuum. After vacuum distillation (0.2 mmHg), 40.5 g (yield: 86%) of 4-(3-trimethylsilanylpropyloxy)benzaldehyde are obtained in the form of a colorless oil which distils at 110–114° C. and which is used as it is in the next step.

b) Second Step: Preparation of the Derivative of Example 1:
(Phenylsulfonyl)acetonitrile (4 g, 22.1 mmol) and the preceding derivative (5.22 g, 22.1 mmol) are dissolved in 40 ml of absolute ethanol and heated under reflux in the presence of a catalytic quantity of piperidine (0.5 ml) for 48 hours.

The reaction medium is cooled to room temperature and the precipitate formed is filtered and washed with cold ethanol. After drying in a dessicator, 8.82 g (yield 82%) of the derivative of Example 1 are obtained in the form of a pale yellow solid.

Melting point: 74° C. ¹H NMR (DMSO-d6, 400 MHZ, δ ppm): 8.46 (s, 1H); 8.04 (d, 2H); 8.01 (d, 2H); 7.81 (t, 1H); 7.73 (m, 2H); 7.15 (d, 2H); 4.06 (m, 2H); 1.73 (m, 2H); 0.58 (m, 2H); 0.01 (s, 9H). ¹³C NMR (DMSO-d6, 100 MHZ, δ ppm): 165.5; 154.3; 139.9; 136.5; 135.6; 131.7; 129.5; 124.2; 117.3; 115.6; 110.7; 72.4; 24.8; 13.6; 0. UV (EtOH), λmax=347 nm; εmax=32 500; E1%=813.

Example 2

Synthesis of [4-[2-methyl-3-[1,3,3,3-tetramethyl-1-[(trimethylsilyl)oxy]disiloxanyl]propyloxy]phenyl]-2-(benzenesulfonyl)acrylonitrile (compound A) of Formula (1) with $R_1$ to $R_3$=H, s=1, r=0 and B=R=$CH_3$, L is of formula (a) with Y=$CH_3$, Z=$CH_2$ and p=1:

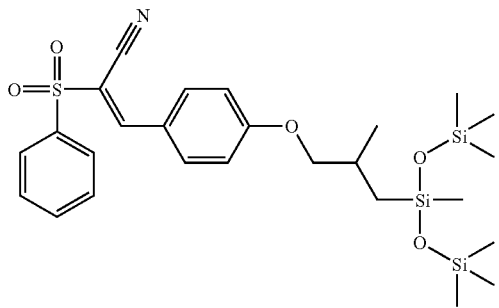
(compound A)

a) First Step: Preparation of 2-benzenesulfonyl-3-[4-(2-methylallyloxy)phenyl]acrylonitrile:

A solution of 4-(2-methylallyloxy)-benzaldehyde (7.03 g, 40 mmol) and of (phenylsulfonyl)acetonitrile (7.24 g, 40 mmol) in 70 ml absolute ethanol is heated under reflux in the presence of a catalytic quantity of piperidine (0.5 ml) for 48 hours. The reaction medium is cooled to room temperature and the precipitate formed is filtered and washed with cold ethanol. After drying in a dessicator, 10.45 g (yield 77%) of 2-benzenesulfonyl-3-[4-(2-methylallyloxy)phenyl]acrylonitrile are obtained in the form of a very pale yellow solid which is used as it is in the next step.

¹H NMR (DMSO-d6, 400 MHZ, δ ppm): 8.44 (s, 1H); 8.04 (d, 2H); 8.00 (d, 2H); 7.82 (m, 1H); 7.73 (m, 2H); 7.18 (d, 2H); 5.00 (d, 2H); 4.61 (s, 2H); 1.76 (s, 3H). ¹³C NMR (DMSO-d6, 100 MHZ, δ ppm): 163.3; 152.6; 140.0; 138.2; 134.8; 133.7; 130.0; 127.8; 122.7; 115.8; 113.8; 112.8; 109.3; 71.3; 19.0. UV (EtOH), λmax=345 nm; εmax=000, E1%=736.

b) Second Step: Preparation of the derivative of Example 2:

Heptamethyltrisiloxane (6 g, 27 mmol) is added, over 30 minutes, to a solution of the preceding derivative (7.5 g, 22.1 mmol) and of platinum catalyst (complex containing 3–3.5% by weight of Pt in cyclovinylmethylsiloxane from Hüls Petrarch PC085, 50 µl) in ml of dry toluene heated to 70° C. The reaction medium is kept for 6 hours at this temperature. The mixture is then concentrated and the oil obtained is separated by chromatography on a silica gel column, eluting with the heptane/ethyl acetate 4/1 mixture.

4.8 g (yield 55%) of the derivative of Example 2 are obtained in the form of a yellow oil. $^1$H NMR (DMSO-d6, 400 MHZ, δ ppm): 8.43 (s, 1H); 8.01 (dd, 4H); 7.82 (m, 1H); 7.73 (m, 2H); 7.13 (d, 2H); 3.91–3.85 (m, 2H); 2.05 (m, 1H); 1.02 (d, 3H); 0.72 (dd, 1H); 0.42 (m, 1H); 0.07 (s, 18H); 0.04 (s, 3H). $^{13}$C NMR (DMSO-d6, 100 MHZ, δ ppm): 162.1; 150.8; 136.4; 133; 132; 128.2; 126; 120.7; 113.7; 112; 107.3; 73; 26.5; 19.5; 17.4; 0; –1.0. UV (EtOH), λmax=348 nm; εmax=35 500, E1%=632.

Example 3

Synthesis of the Mixture [4-[3-[1,3,3,3-tetramethyl-1-[(trimethylsilyl)oxy]disiloxanyl]-2-propenoxy]phenyl]-2-(benzenesulfonyl)acrylonitrile (Compound B) and [4-[2-[1,3,3,3-tetramethyl-1-[(trimethylsilyl)oxy]-disiloxanyl]-2-propenoxy]phenyl]-2-(benzenesulfonyl)-acrylonitrile (Compound C) of Formula (1) with $R_1$ to $R_3$=H, s=1, r=0 and B=R=CH$_3$, L is of Formula (a') with Y=H, Z=CH$_2$ and p=1:

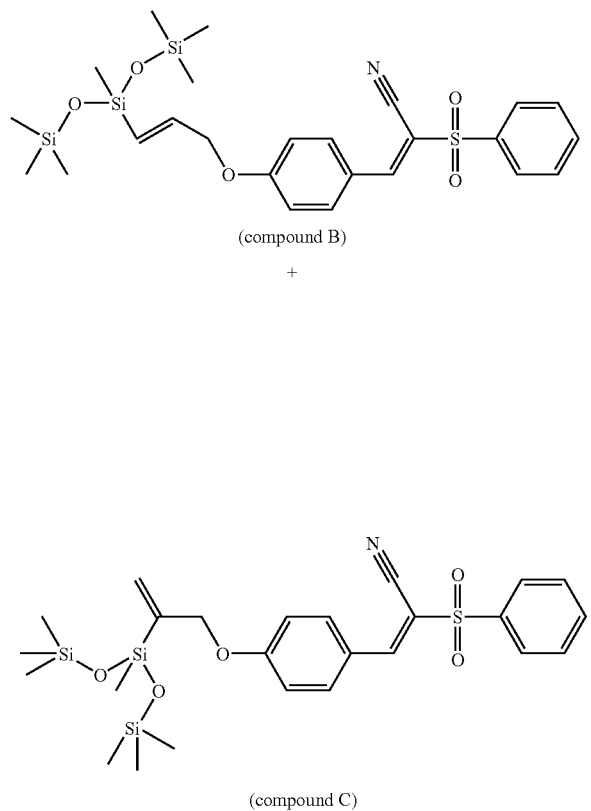

(compound B)

+

(compound C)

a) First Step: Preparation of prop-2-ynyloxybenzaldehyde:

A solution of 4-hydroxybenzaldehyde (1 g, 8.2 mmol), of potassium carbonate (2.27 g, 16.4 mmol) and of propargyl bromide (1.4 ml of a solution at 80% in toluene) in 50 ml of anhydrous acetone is heated under reflux for 5 hours. The reaction medium is cooled to room temperature, filtered and concentrated. The crude reaction product obtained is purified using a chromatography column on silica gel, eluting with dichloromethane. 1.31 g (quantitative yield) of prop-2-ynyloxybenzaldehyde are obtained in the form of a white solid which is used as it is in the next step. $^1$H NMR (DMSO-d6, 400 MHZ, δ ppm): 9.89 (s, 1H); 7.89 (d, 2H); 7.18 (d, 2H); 4.95 (s, 2H); 3.65 (s, 1H).

b) Second Step: Preparation of benzenesulfonyl-3-(4-prop-2-ynyloxyphenyl)acrylonitrile:

A solution of the preceding product (1.3 g, 8.12 mmol) and of (phenylsulfonyl)acetonitrile (1.47 g, 8.1 mmol) in 8 ml of absolute ethanol is heated under reflux for 12 hours in the presence of a catalytic quantity of piperidine (0.2 ml). The medium is then cooled to 0° C. and filtered. The solid obtained is washed with 2 ml of cold absolute ethanol. 2.16 g (yield 82%) of benzenesulfonyl-3-(4-prop-2-ynyloxyphenyl)acrylonitrile are obtained in the form of a cream-white solid. $^1$H NMR (DMSO-d6, 400 MHZ, δ ppm): 8.47 (s, 1H); 8.08 (d, 2H); 8.06 (m, 2H); 7.83 (m, 1H); 7.76 (m, 2H); 7.20 (d, 2H); 4.95 (s, 2H); 3.66 (s, 1H). $^{13}$C NMR (DMSO-d6, 100 MHZ, δ ppm): 162.4; 153.0; 138.5; 135.2; 134.0; 130.5; 128.3; 123.7; 116.3; 114.1; 110.2; 579.4; 78.6; 56.4.

c) Third Step: Preparation of the product of Example 3:

Heptamethyltrisiloxane (1.02 ml, 3.7 mmol) is added, over 5 minutes, to a solution of the preceding product (1 g, 3.07 mmol) and of platinum catalyst (complex containing 3–3.5% by weight of Pt in cyclovinylmethylsiloxane from Hüls Petrarch PC085, 7 μl) in 10 ml of dry toluene at 70° C. The reaction medium is kept for 19 hours at this temperature. The mixture is then concentrated and separated by chromatography on a silica gel column, eluting with the heptane/ethyl acetate 4/1 mixture. 1.51 g (yield 90%) of the mixture of the 2 derivatives of Example 3 are obtained in the form of a yellow oil and in a 33:67 ratio as seen in the following $^1$H NMR spectrum: $^1$H NMR (DMSO-d6, 400 MHZ, δ ppm): 8.44 (s, 1H); 8.04 (m, 2H); 8.00 (d, 2H); 7.82 (t, 1H); 7.73 (t, 2H); 7.14 (t, 2H); 6.26 (dt, 0.33H, Htrans); 5.88 (m, 0.67H, Hcis); 5.85 (dt, 0.33H, Htrans); 5.62 (m, 0.67H, Htrans); 4.78 (dd, 0.66H, CH$_2$trans); 4.74 (s, 1.32H, CH$_2$cis); 0.15 (s, 2H); 0.07 (s, 14H); 0.04 (s, 6H).

$^{13}$C NMR (DMSO-d6, 100 MHZ, δ ppm): 163.3; 152.6; 144.7; 138.2; 134.8; 133.7; 130.05; 129.3; 127.8; 122.7; 115.8; 113.8; 109.3; 71.2; 1.7; 0.11. UV (EtOH), λmax=345 nm; εmax=33 000, E1%=610.

Example 4

Synthesis of the Mixture of Three Compounds Having the Random α,ω-polydimethylsiloxane Structure®=7) Carrying 2 Groups 4-(2-propenoxyphenyl)-2-(benzenesulfonyl)acrylonitrile and/or 4-(3-propenoxyphenyl)-2-(benzenesulfonyl) acrylonitrile of Formula (1) with $R_1$ to $R_3$=H, s=0, r=7 and B=R=CH$_3$, L is of Formula (a') with Y=H, Z=CH$_2$ and p=1:

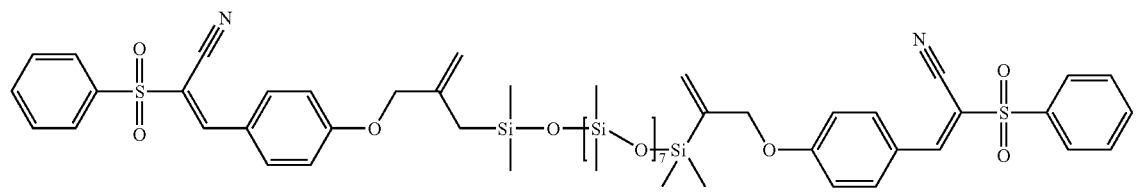

(compound D)

+

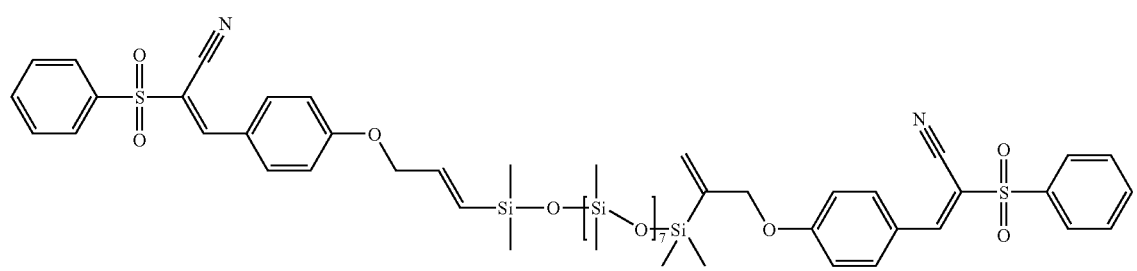

(compound E)

+

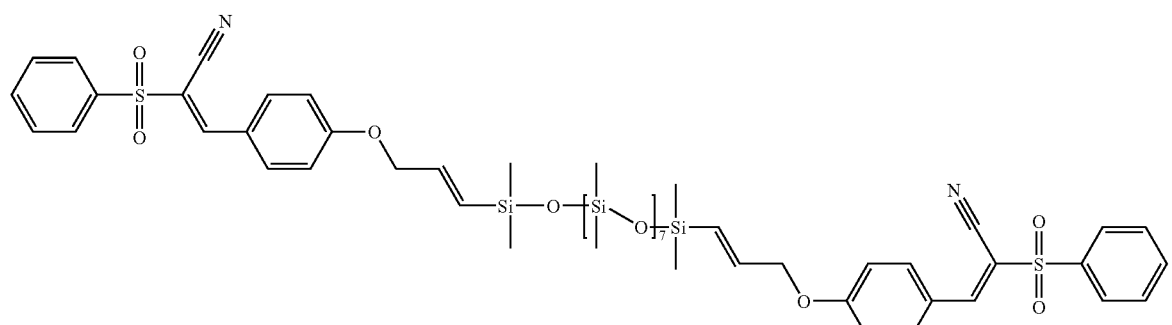

(compound F)

1.51 ml of random α,ω-dihydropolydimethylsiloxane®=7) (2.1 meq as SiH) are added, over 7 minutes, to a solution of benzenesulfonyl-3-(4-prop-2-ynyloxyphenyl)acrylonitrile (1.15 g, 3.56 mmol) prepared in the second step of Example 3 and of platinum catalyst (complex containing 3–3.5% by weight of Pt in cyclovinylmethylsiloxane from Hüls Petrarch PC085, 7 μl) in 10 ml of dry toluene at 70° C. The reaction medium is kept for 21 hours at this temperature. The mixture is then concentrated and separated by chromatography on a silica gel column, eluting with the heptane/ethyl acetate 9/1 mixture. 1.21 g (yield 54%) of the product of Example 4 are obtained in the form of a yellow oil:

$^{13}$C NMR (DMSO-d6, 100 MHZ, δ ppm): 163.3; 152.5; 146.0; 138.2; 134.8; 133.8; 130.0; 127.8; 126.8; 122.7; 115.7; 113.8; 109.3; 71.3; 1.03; 0.95; 0.4. UV (EtOH), λmax=345 nm, E1%=510.

EXAMPLES OF FORMULATION

Example 1

Mixture Glyceryl Mono/Distearate/Polyethylene

| | |
|---|---|
| glycol stearate 100 EO (ARLACEL 165 FL-ICI) | 1.0 g |
| Cetyl alcohol | 0.5 g |
| Stearic acid from palm oil | 2.5 g |
| (STEARINE TP-STEARINERIE DUBOIS) | |
| Polydimethylsiloxane | 0.5 g |
| (DOW CORNING 200 FLUID-DOW CORNING) | |
| $C_{12}/C_{15}$ alcohol benzoate | 20 g |
| (WITCONOL TN-WITCO) | |
| Compound G | 0.5 g |
| Glycerine | 5.0 g |
| Hexadecyl alcohol phosphate, potassium salt | 1.0 g |
| (AMPHISOL K-HOFFMANN LA ROCHE) | |

-continued

| | |
|---|---|
| Polyacrylic acid (SYNTHALEN K-3V) | 0.3 g |
| Hydroxypropylmethylcellulose (METHOCEL F4M-DOW CHEMICAL) | 0.1 g |
| Cyclopentadimethylsiloxane (DC245-DOW CORNING) | 2.0 g |
| Triethanolamine | 0.8 g |
| Preservatives | qs |
| Demineralized water | qs 100 g |

Example 2

| | |
|---|---|
| Mixture of cetylstearyl alcohol and oxyethylenated cetyisteraryl alcohol containing 33 EO (80/20) (SINNOWAX AO-HENKEL) | 7.0 g |
| Mixture of glyceryl mono- and distearate (CERASYNT SD-V from ISP) | 2.0 g |
| Cetyl alcohol | 1.5 g |
| Polydimethylsiloxane (DOW CORNING 200 FLUID-DOW CORNING) | 1.5 g |
| $C_{12}/C_{15}$ alcohol benzoate (WITCONOL TN-WITCO) | 8.0 g |
| Liquid paraffin | 10.0 g |
| Compound A | 2.0 g |
| Glycerine | 10.0 g |
| Preservatives | qs |
| Demineralized water | qs 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A siloxane/silane compound having one of the following structural formulae (1), (2) or (3):

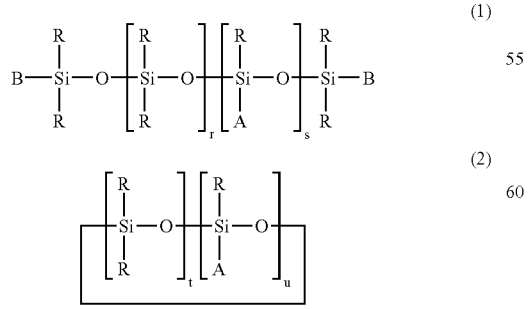

in which A is a radical of the following formula (I):

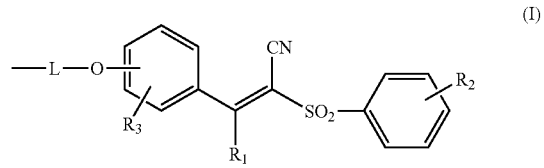

or its trans isomer form; $R_1$ is a hydrogen atom, a saturated or unsaturated, linear or branched $C_1$–$C_8$ alkyl radical, or a phenyl radical which is optionally substituted with one or more saturated or unsaturated, linear or branched $C_1$–$C_8$ alkyl or alkoxy radicals; $R_2$ is a hydrogen atom, a saturated or unsaturated, linear or branched $C_1$–$C_8$ alkyl radical, or a saturated or unsaturated, linear or branched $C_1$–$C_8$ alkoxy radical; $R_3$ is a saturated or unsaturated, linear or branched $C_1$–$C_8$ alkyl radical, or a saturated or unsaturated, linear or branched $C_1$–$C_8$ alkoxy radical; L is a divalent radical bonding the radical A directly onto the siloxane or silane backbone, said divalent radical being methylene, ethylene or a group having one of the following formulae (a), (a') or (a"):

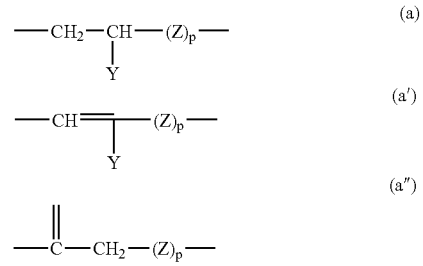

in which Z is a saturated or unsaturated, linear or branched $C_1$–$C_6$ alkylene radical optionally substituted with a hydroxyl radical, or a saturated or unsaturated, linear or branched $C_1$–$C_8$ alkyl radical; Y is a hydrogen atom, a hydroxyl radical, or a saturated or unsaturated, linear or branched $C_1$–$C_8$ alkyl radical; p is 0 or 1; the radicals R, which are identical or different, are each a saturated or unsaturated, linear or branched $C_1$–$C_{20}$ alkyl radical, a phenyl radical, a 3,3,3-trifluoropropyl radical, or a trimethylsilyloxy radical, at least 80% by number of the radicals R being methyl; the radicals B, which are identical or different, are each a radical R or a radical A; r is a number varying from 0 to 50; s is a number varying from 0 to 20 and, if s is 0, at least one of the two radicals B is a radical A; u is a number varying from 1 to 6 inclusive; t is a number varying from 0 to 10; t+u is greater than or equal to 3; and the radicals $R'_1$, $R'_2$, $R'_3$, which are identical or different, are each a saturated or unsaturated, linear or branched $C_1$–$C_8$ alkyl radical; phenyl radical, or a benzyl radical; or mixture thereof.

2. A siloxane/silane compound as defined by claim 1, having the formula (2) and at least one of the following characteristics:

R is alkyl;

t+u ranges from 3 to 5;

$R_1$ is H;

R₂ is H;
R₃ is H;
p equals 1;
Z is CH₂;
Y is H or CH₃.

3. A siloxane/silane compound as defined by claim 1, having the formula (1) and at least one of the following characteristics:
R is alkyl;
B is alkyl;
r varies from 0 to 10, inclusive;
s varies from 0 to 6, inclusive;
R₁ is H;
R₂ is H;
R₃ is H;
p equals 1;
Z is CH₂;
Y is H or CH₃.

4. A siloxane/silane compound as defined by claim 3, being [4-[2-methyl-3-[1,3,3,3-tetramethyl-1-[(trimethylsilyl)oxy]disiloxanyl]-propyloxy]phenyl]-2-(benzenesulfonyl)acrylonitrile having the structural formula:

(compound A)

5. Admixture of compounds as defined by claim 3, comprising a mixture of [4-[3-[1,3,3,3-tetramethyl- 1-[(trimethylsilyl )-oxy]disiloxanyl]-2-propenoxy]phenyl]-2-(benzenesulfonyl)acrylonitrile (compound B) and [4-[2-[1,3,3,3-tetramethyl-1-[(trimethylsilyl)oxy]-disiloxanyl]-2-propenoxy]phenyl]-2-(benzenesulfonyl)acrylonitrile (compound C) having the following structural formulae:

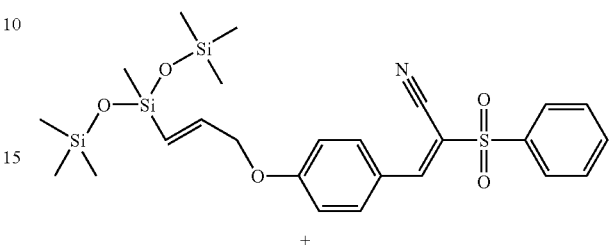

(compound B)

(compound C)

6. Admixture of compounds as defined by claim 3, comprising a mixture of 3 α,ω-polydimethylsiloxane compounds substituted by 2 groups 4-(2- propenoxyphenyl)-2-(benzenesulfonyl)acrylonitrile and/or 4-(3-propenoxyphenyl)-2-(benzenesulfonyl)acrylonitrile having the following structural formulae:

(compound D)

+

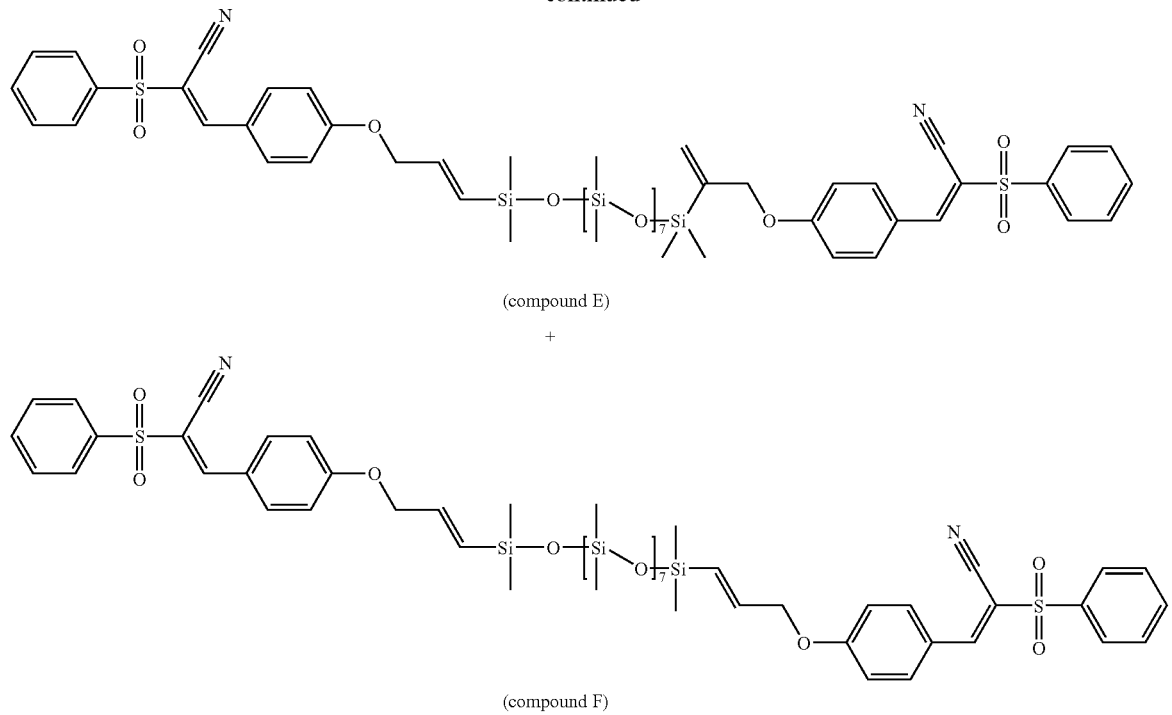

(compound E)

+

(compound F)

7. A siloxane/silane compound as defined by claim 1, or mixture thereof, having the formula (3) and at least one of the following characteristics:

$R'_1$ is methyl;
$R'_2$ is methyl;
$R'_3$ is methyl;
$R_1$ is H;
$R_2$ is H;
$R_3$ is H;
p equals 1;
Z is $CH_2$; and
Y is H or $CH_3$.

8. A siloxane/silane compound as defined by claim 7, comprising 2-benzenesulfonyl-3-[4-(3-trimethylsilanylpropoxy)phenyl]acrylonitrile having the following structural formula:

(compound G)

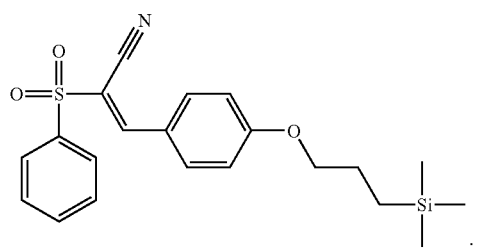

9. A topically applicable cosmetic/dermatological composition suited for photoprotecting the skin and/or the hair against the damaging effects of UV-irradiation, comprising at least one compound or mixture of compounds of formula (1), (2) or (3) as defined by claim 1, formulated into a topically applicable, cosmetically acceptable carrier therefor.

10. The cosmetic/dermatological composition as defined by claim 9, said compound(s) of formula (1), (2) or (3) comprising from 0.1% to 20% by weight thereof.

11. The cosmetic/dermatological composition as defined by claim 9, further comprising one or more additional organic sunscreens which are active in the UV-A and/or UV-B region.

12. The cosmetic/dermatological composition as defined by claim 11, said at least one additional organic UV-screening agent being selected from the group consisting of anthranilates; cinnamic derivatives; dibenzoylmethane derivatives; salicylic derivatives; camphor derivatives; triazine derivatives; benzophenone derivatives; β,β'-diphenyl acrylate derivatives; benzotriazole derivatives; benzimidazole derivatives; imidazolines; bis-benzoazolyl derivatives; p-aminobenzoic acid (PABA) derivatives; methylenebis(hydroxyphenylbenzotriazole) derivatives; screening polymers and screening silicones other than those of formula (1), (2) or (3); dimers derived from α-alkylstyrene; 4,4-diarylbutadiene derivatives; and mixtures thereof.

13. The cosmetic/dermatological composition as defined by claim 12, said at least one additional organic UV-screening agent being selected from the group consisting of Ethylhexyl Salicylate, Butyl Methoxydibenzoylmethane, Ethylhexyl Methoxycinnamate, Octocrytene, Phenylbenzimidazole Sulfonic Acid, Terephthalylidene Dicamphor Sulfonic Acid, Benzophenone-3, Benzophenone-4, Benzophenone-5, n-Hexyl 2-(4-diethylamino-2-hydroxybenzoyl) benzoate, 4-Methylbenzylidene camphor, Disodium Phenyl Dibenzimidazole Tetra-sulfonate, Anisotriazine, Ethylhexyl triazone, Diethylhexyl Butamido Triazone, 2,4,6-Tris(diisobutyl 4'-aminobenzalmalonate)-s-triazine, Methylene bis-Benzotriazolyl Tetramethylbutyiphenol, Drometrizole Trisiloxane, 1,1 -dicarboxy (2,2'-dimethyl-propyl)-4,4-diphenylbutadiene and mixtures thereof.

14. The cosmetic/dermatological composition as defined by claim 9, said at least one additional organic UV-screening agent comprising from 0.2% to 15% by weight thereof.

15. The cosmetic/dermatological composition as defined by claim 9, further comprising one or more coated or uncoated UV-screening pigments or nanopigments of metal oxides.

16. The cosmetic/dermatological composition as defined by claim 15, said metal oxides comprising titanium oxides in amorphous form, iron oxides, zinc oxides, zirconium oxides, cerium oxides and mixtures thereof.

17. The cosmetic/dermatological composition as defined by claim 9, further comprising one or more agents for artificially bronzing and/or tanning the skin.

18. The cosmetic/dermatological composition as defined by claim 9, further comprising one or more cosmetic adjuvants selected from the group consisting of fatty substances, organic solvents, ionic and nonionic thickeners, demulcents, humectants, antioxidants, moisturizers, desquamating agents, anti-free-radical agents, antipollution agents, antibacterials, anti-inflammatory agents, depigmenting agents, propigmenting agents, opacifiers, stabilizers, emollients, silicones, anti-foaming agents, insect repellents, perfumes, preservatives, anionic, cationic, nonionic, zwitterionic and amphoteric surfactants, substance P antagonists, substance CGRP antagonists, fillers, pigments, colorants, polymers, propellants, alkalinizing and acidifying agents.

19. The cosmetic/dermatological composition as defined by claim 9, formulated as a nonionic vesicular dispersion, an emulsion, a cream, a milk, a gel, a gel cream, a suspension, a dispersion, a powder, a solid stick, a mousse or a spray.

20. The cosmetic/dermatological composition as defined by claim 9, formulated as a makeup for the nails, the lips, the eyelashes, the eyebrows or the skin and provided in an anhydrous or aqueous, solid or pasty form, or in the form of an emulsion, a suspension or a dispersion.

21. A cosmetic/dermatological composition as defined by claim 9, formulated for protecting the hair against ultraviolet rays and provided as a shampoo, a lotion, a gel, an emulsion or a nonionic vesicular dispersion.

22. A regime or regimen for photoprotecting the skin and/or the hair of a subject whose skin and/or hair is in need of photoprotection against the damaging effects of UV-radiation, comprising topically applying thereon an effective amount of the cosmetic/dermatological composition as defined by claim 9.

23. A regime or regimen for photoprotecting the skin and/or the hair of a subject whose skin and/or hair is in need of photoprotection against the damaging effects of UV-A solar radiation, comprising topically applying thereon an effective amount of the cosmetic/dermatological composition as defined by claim 9.

* * * * *